(12) United States Patent
McCord et al.

(10) Patent No.: US 9,891,207 B2
(45) Date of Patent: Feb. 13, 2018

(54) PAPER MICROFLUIDIC DEVICES FOR DETECTION OF IMPROVISED EXPLOSIVES

(71) Applicants: Bruce McCord, Miami, FL (US); Inge Corbin, Doral, FL (US); Lucas Blanes, Sydney (AU)

(72) Inventors: Bruce McCord, Miami, FL (US); Inge Corbin, Doral, FL (US); Lucas Blanes, Sydney (AU)

(73) Assignee: The Florida International University Board of Trustees, Miami, FL (US)

( * ) Notice: Subject to any disclaimer, the term of this patent is extended or adjusted under 35 U.S.C. 154(b) by 577 days.

(21) Appl. No.: 14/216,869

(22) Filed: Mar. 17, 2014

(65) Prior Publication Data

US 2016/0139102 A1    May 19, 2016

Related U.S. Application Data

(60) Provisional application No. 61/794,955, filed on Mar. 15, 2013.

(51) Int. Cl.
*G01N 21/00* (2006.01)
*G01N 21/65* (2006.01)
*G01N 33/22* (2006.01)
*B01L 3/00* (2006.01)

(52) U.S. Cl.
CPC .......... *G01N 33/227* (2013.01); *B01L 3/5023* (2013.01); *B01L 3/5027* (2013.01); *B01L 2200/10* (2013.01); *B01L 2200/12* (2013.01); *B01L 2300/0825* (2013.01); *B01L 2300/0864* (2013.01); *B01L 2300/0887* (2013.01); *B01L 2300/126* (2013.01); *B01L 2300/165* (2013.01)

(58) Field of Classification Search
CPC .............................. G01N 21/00; G01N 21/65
See application file for complete search history.

(56) References Cited

U.S. PATENT DOCUMENTS

2010/0210029 A1* 8/2010 Meinhart ............... G01N 21/05
                                                                436/168
2011/0111517 A1* 5/2011 Siegel ............... B01L 3/502707
                                                                436/164

OTHER PUBLICATIONS

Bottegal, Megan et al., "Analysis of Ascorbic Acid-Based Black Powder Substitutes by High Performance Liquid Chromatography/Electrospray Ionization-Quadruple Time-of-Flight Mass Spectrometry (HPLC-ESI-QToFMS)," *Rapid Communications in Mass Spectrometry*, 2010, 24(9):1377-1386.
Carrilho, Emanuel, et al., Understanding wax printing: A simple micropatterning process for paper-based microfluidics, *Analytical Chemistry*, 2009, 81(16):7091-7095.
Collin, Olivier L., et al., "Fast Gas Chromatography of Explosive Compounds using a Pulsed Discharge Electron Capture Detector," *Journal of Forensic Sciences*, 2006, 51(4):815-818.

(Continued)

*Primary Examiner* — Aileen B Felton
(74) *Attorney, Agent, or Firm* — Saliwanchik, Lloyd & Eisenschenk

(57) ABSTRACT

Paper microfluidic devices for testing for explosives are provided, along with methods of fabricating and using the same. One or more channels are formed on a paper substrate, and a test spot is formed in at least one of the channels. The channels can be hydrophobic. A test reagent is provided in the test spot and tests for explosives.

14 Claims, 10 Drawing Sheets

(56) References Cited

OTHER PUBLICATIONS

De Perre, Chloé et al., "Rapid and specific detection of urea nitrate and ammonium nitrate by electrospray ionization time-of-flight mass spectrometry using infusion with crown ethers," *Rapid Communications in Mass Spectrometry*, 2011, (26):154-162.

De Perre, Chloé, et al., "Trace analysis of urea nitrate by liquid chromatography-UV/fluorescence," *Forensic Science International*, 2011, 211(1):76-82.

Doctor, Erika L., et al., "Comparison of Aggregating Agents for Surface-Enhanced Raman Analysis of Benzodiazepines," *64th Annual meeting American Academy of Forensic Sciences*, Feb. 2012.

Doyle, Janet M., et al., "A Multicomponent Mobile Phase for Ion Chromatography Applied to the Separation of Anions from the Residue of Low Explosives," *Analytical Chemistry*, 2000, 72(10):2303-2307.

Doyle, Janet M., et al., "Novel electrolyte for the analysis of cations in low explosive residue by capillary electrophoresis," *Journal of Chromatography B*, 1998, (714):105-111.

Dungchai, Wijitar, et al., "A low-cost, simple, and rapid fabrication method for paper-based microfluidics using wax screen-printing," *Analyst*, 2011, (136):77-82.

Dungchai, Wijitar, et al., "Use of multiple colorimetric indicators for paper-based microfluidic devices," *Analytica Chimica Acta*, 2010, (674):227-233.

Heramb, Robert M., et al., "The manufacture of smokeless powders and their forensic analysis: a brief review," *Forensic Science Communications*, 2002, 4(2):1-5.

Hopper, Kristy G., et al., "A Novel Method for Analysis of Explosives Residue by Simultaneous Detection of Anions and Cations via Capillary Zone Electrophoresis," *Talanta*, 2005, 67(2):304-312.

Lahoda, Kristy G., et al., "A Survey of Background Levels of Explosives and Related Compounds in the Environment," *Journal of Forensic Sciences*, 2008, 53(4):802-806.

Li, Xiaokun, et al., "Gold nanoparticle-based colorimetric assay for selective detection of aluminum cation on living cellular surfaces," *Chem. Commun.*, 2010, (46):988-990.

Lu, Yao, et al., "Rapid prototyping of paper-based microfluidics with wax for low-cost, portable bioassay," *Electrophoresis*, 2009, (30):1-4.

Martinez, Andres W., et al., "Diagnostics for the Developing World: Microfluidic Paper-Based Analytical Devices," *Analytical Chemistry*, Jan. 2010, 82(1):3-10.

Martinez, Andres W., et al., "Patterned paper as a platform for inexpensive, low-volume, portable bioassays," *Angew. Chem. Int. Ed.* 2007, (46):1318-1320.

Mathis, John A., et al., "Gradient Reversed-Phase Liquid Chromatographic-Electrospray Ionization Mass Spectrometric Method for the Comparison of Smokeless Powders," *Journal of Chromatography A*, 2003, (988):107-116.

Mathis, John A., et al., "The Analysis of High Explosives by Liquid Chromatography/Electrospray Ionization Mass Spectrometry: Multiplexed Detection of Negative Ion Adducts," *Rapid Communications in Mass Spectrometry*, 2005, 19(2):99-104.

McCord, Bruce et al., "Chromatography of Explosives: In Forensic Investigations of Explosives," 2nd Edition, Beveridge, A. D., Ed. Taylor and Francis, Boca Raton FL. 2012, p. 585-620.

McCord, Bruce et al., "Forensic Analysis of Explosives using Ion Chromatographic Methods," *Analytica Chimica Acta*, 1994, (288):43-56.

McCord, Bruce et al., "The Analysis and Characterization of TNT using Liquid Chromatography with Photodiode Array Detection," *Journal of Forensic Sciences*, 1992, 37(6):1574-1584.

Smith, Kelly D., et al., "Detection of Smokeless Powder Residue on Pipe Bombs by Micellar Electrokinetic Capillary Electrophoresis," *Journal of Forensic Sciences*, 1999, 44(4):789-794.

Tarvin, Megan, et al., "Analysis of Hydrogen Peroxide Field Samples by HPLC/FD and HPLC/ED in DC Mode," *Forensic Science International*, 2011, 209(1-3):166-72.

Tarvin, Megan, et al., "Optimization of Two Methods for the Analysis of Hydrogen Peroxide: High Performance Liquid Chromatography with Fluorescence Detection and High Performance Liquid Chromatography with Electrochemical Detection in Direct Current Mode," *Journal of Chromatography A*, 2010, 1217(48):7564-7572.

Thomas, Jennifer L., et al., "Separation and Detection of Smokeless Powder Additives by Ultra Performance Liquid Chromatography with Tandem Mass Spectrometry," (UPLC/MS/MS), *Journal of Forensic Sciences*, 2013, 58(3):609-615.

Wissinger, Chad E., et al., "A reversed phase HPLC procedure for smokeless powder comparison," *Journal of Forensic Sciences*, 2002, 47(1):168-174.

Li, Xiaokun, et al., "Gold nanoparticle-based calorimetric assay for selective detection of aluminum cation on living cellular surfaces," *Chem. Commun.*, 2010, (46):988-990.

\* cited by examiner

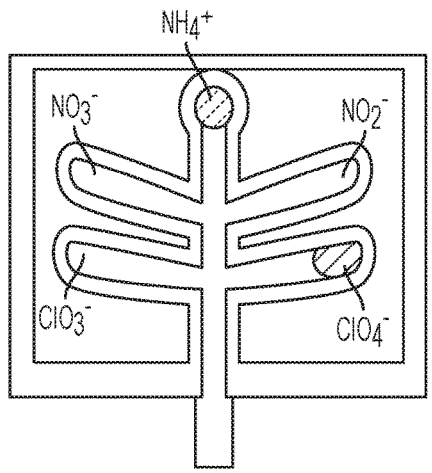
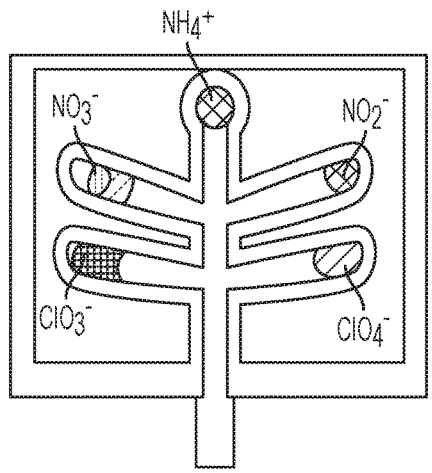
FIG. 10A    FIG. 10B
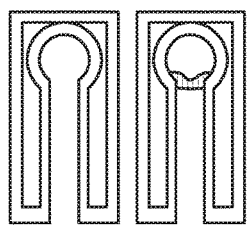
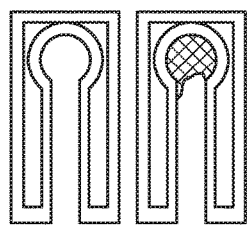
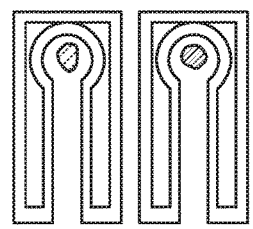
FIG. 11A    FIG. 11B    FIG. 11C
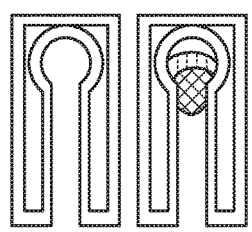
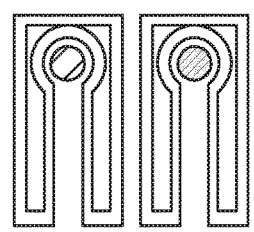
FIG. 11D    FIG. 11E

PAPER MICROFLUIDIC DEVICES FOR DETECTION OF IMPROVISED EXPLOSIVES

CROSS REFERENCE TO RELATED APPLICATION

The present application claims the benefit of U.S. Provisional Application Ser. No. 61/794,955, filed Mar. 15, 2013, which is hereby incorporated by reference herein in its entirety, including any figures, tables, and drawings.

GOVERNMENT SUPPORT

The subject invention was made with government support under a research project supported by National Institute of Justice Award No. NIJ 20012-90426-FL-DN. The government has certain rights in this invention.

BACKGROUND

Improvised or homemade explosives (HMEs) were once limited to war zones but have recently become a concern for law enforcement and other first responders in the United States and abroad. Such responders may encounter organized groups or curious "citizen scientists" synthesizing HMEs. Fast and accurate identification of the explosive compound used is of the utmost importance. Common constituents of HMEs include organic and inorganic compounds, sugars, and elemental metals. Many different analytical technologies exist for detecting and quantifying explosive materials; however, the different unregulated and easily obtained compounds used in the devices vary greatly in molecular mass, structure, and physicochemical properties, and no single analytical instrument has the capability to identify them all.

A number of different techniques are available for the identification of explosive compounds. Gas chromatography/mass spectrometry (GC/MS), liquid chromatography/mass spectrometry (LC/MS), or Fourier transform infrared spectroscopy (FT-IR) may be used for organic and inorganic compounds while ion chromatography (IC) and capillary electrophoresis (CE) may be used for inorganic ions. Metals can be detected by scanning electron microscopy with energy-dispersive X-ray spectroscopy (SEM/EDS) or by X-ray diffraction (XRD). Some compounds require electrospray ionization mass spectroscopy (ESI-MS) to be identified in a sample. These detection techniques have similar shortcomings; they require large, expensive pieces of instrumentation that, with the exception of FT-IR, are not portable. Due to vacuum, power, and gas requirements, the instruments required for these techniques are necessarily centrally located. Thus, the sample must be collected and brought to the laboratory, thereby increasing the amount of time before any analytical information on the identity of the explosive can be obtained and, e.g., provided to first responders.

Additionally, samples may need to undergo preparative techniques, such as filtration or extraction before instrumental analysis can be performed, thereby increasing the total analysis time. This also increases the potential for analytes to be lost through such processes by adsorption onto the filtration medium or degradation of the sample by interaction with the extraction solvent. Samples must also be prepared in sufficient volume (generally at least 200 µL per instrument) to be handled by an auto-sampler.

BRIEF SUMMARY

The subject invention provides devices and methods for detection of explosives, e.g., improvised explosives or homemade explosives (HMEs). In one embodiment, a paper microfluidic device (PMD) can be used to detect explosives, such as improvised explosives and/or HMEs.

In an embodiment, a PMD of the subject invention includes one or more hydrophobic channels on a paper substrate and a test reagent provided at a test spot of at least one of the hydrophobic channels. The test reagent is configured or adapted to test for one or more improvised explosives or HMEs. The test spot can be a colorimetric test spot.

In another embodiment, the subject invention provides a method of testing a sample for explosives (e.g., improvised explosives and/or HMEs), wherein the method includes providing the sample to a PMD. The PMD includes one or more hydrophobic channels on a paper substrate and a test reagent provided at a test spot of at least one of the hydrophobic channels. The test reagent is configured or adapted to test for improvised explosives or HMEs. The sample can be provided to the PMD in a very small amount (e.g., 50 µL or less). For example, the sample can be provided to the PMD in a volume of 35 µL or about 35 µL.

In yet another embodiment, the subject invention provides a method of fabricating a PMD, wherein the method includes printing a wax pattern onto a paper substrate (e.g., filter paper or chromatography paper) and heating the paper substrate, thereby allowing the liquid wax to penetrate the paper substrate. One or more test reagents can be provided to test spots in the channels formed by the wax. The test reagent is configured or adapted to test for improvised explosives or HMEs.

In yet another embodiment, the subject invention provides a kit that includes a PMD. The PMD includes one or more hydrophobic channels on a paper substrate. The PMD may have test reagents already present for spot tests or may have no test reagents present on the PMD. The kit may additionally include one or more test reagents. The test reagents are configured or adapted to test for improvised explosives or HMEs. A user can apply the test reagents to the testing sites of a PMD that does not already have the test reagents present.

BRIEF DESCRIPTION OF THE DRAWINGS

FIG. 10A shows an image of a PMD according to an embodiment of the subject invention prior to analysis.

FIG. 10B shows an image of a PMD according to an embodiment of the subject invention after analysis.

FIG. 11A shows an image of a PMD according to an embodiment of the subject invention.

FIG. 11B shows an image of a PMD according to an embodiment of the subject invention.

FIG. 11C shows an image of a PMD according to an embodiment of the subject invention.

FIG. 11D shows an image of a PMD according to an embodiment of the subject invention.

FIG. 11E shows an image of a PMD according to an embodiment of the subject invention.

DETAILED DESCRIPTION

Figure 1A:
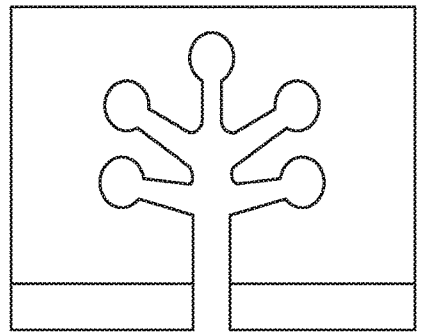
FIGS. 1A-1D show a process of fabricating a paper microfluidic device (PMD) according to an embodiment of the subject invention.

When the term "about" is used herein, in conjunction with a numerical value, it is understood that the value can be in a range of 95% of the value to 105% of the value, i.e. the value can be +/−5% of the stated value. For example, "about 1 kg" means from 0.95 kg to 1.05 kg.

Explosives, such as improvised explosives and homemade explosives (HMEs), can be made from organic compounds, inorganic compounds and ions, sugars, and/or metals. Thus, these compounds are all important in explosives analysis (e.g., improvised explosives analysis). However, no single existing instrument can detect all these groups. Instead, in existing techniques, an unknown sample must be taken through a series of extractions for analysis by different types of instrumentation.

Microfluidics involves the manipulation of fluids on a very small (e.g., nanoliter) scale. Traditional microfluidic techniques use glass or polydimethylsiloxane (PDMS) chips hooked to micro-scale pumps, valves, and power systems to transport a sample and effect separation before reaching a detector such as a laser. By miniaturizing the system and exploiting the properties of fluids at the micro level, the sample volume is reduced, the attendant reagent volume is similarly reduced, and the overall efficiency of the system is increased. PDMS chips must be painstakingly fabricated, resulting in a high attendant cost per chip, and they must be handled gently to avoid breakage. The need for a power system to drive the separation and detect the sample components means a traditional microfluidic system can only be used where electricity and a controlled environment are available.

Microfluidic principles have been applied to paper substrates to create paper microfluidic devices. A wax pattern can be printed onto the surface of filter paper, chromatography paper, or a nitrocellulose membrane, and the paper (or membrane) can be heated so the liquid wax penetrates the paper (or membrane), creating hydrophobic barriers that function as lanes for the liquid sample to move along as it is routed to multiplexed detection zones. An article by Martinez et al. presents microfluidic paper-based analytical devices developed as healthcare diagnostic tools to be used in developing nations that do not possess the infrastructure to maintain typical diagnostic equipment (Martinez et al., Diagnostics for the Developing World: Microfluidic Paper-Based Analytical Devices, *Anal. Chem.*, 2010, 82, 3-10). The Martinez et al. article is hereby incorporated by reference in its entirety.

The following publications also discuss analysis techniques, explosives, or microfluidics: (Carrilho E et al., Understanding wax printing: A simple micropatterning process for paper-based microfluidics, *Anal. Chem.* 2009, (81) 16; 7091-95); (Doctor, E.; McCord, B, Comparison of Aggregating Agents for Surface-Enhanced Raman Analysis of Benzodiazepines, 64$^{th}$ Annual meeting American Academy of Forensic Sciences, Feb. 23, 2012); De Perre C et al., Rapid and specific detection of urea nitrate and ammonium nitrate by electrospray ionization time-of-flight mass spectrometry using infusion with crown ethers, *Rapid Commun. Mass Spectrom.* 2012; 26, 154-162); (Dungchai W et al., A low-cost, simple, and rapid fabrication method for paper-based microfluidics using wax screen-printing. *Analyst* 2011; 136, 77-82); (Dungchai W et al. Use of multiple colorimetric indicators for paper-based microfluidic devices, *Analytica Chimica Acta* 2010; 674, 227-233); (Li X et al., Gold nanoparticle-based colorimetric assay for selective detection of aluminum cation on living cellular surfaces, *Chem. Commun.* 2010; 46, 988-990); Lu Y et al., *Rapid prototyping of paper-based microfluidics with wax for low-cost, portable bioassay*, Electrophoresis 2009; 30, 1497-1500); Martinez A W et al., Patterned paper as a platform for inexpensive, low-volume portable bioassays, *Angew. Chem. Int. Ed.* 2007; 46, 1318-1320); (Bruce McCord; Inge Corbin; Edward Bender, Chromatography of Explosives In *Forensic Investigations of Explosives*, 2$^{nd}$ Edition, Beveridge, A. D., Ed. Taylor and Francis, Boca Raton Fla. 2012, pp. 585-620); (Greaux, J.; Lincoln, D.; McCord, B R., Separation and Detection of Smokeless Powder Additives by Ultra-high Performance Liquid Chromatography with Tandem Mass Spectrometry (UPLC/MS/MS), *J. Forensic Sci.* in press); (De Perre, C., Prado, A. and McCord, B. R. Rapid and specific detection of urea nitrate and ammonium nitrate by electrospray ionization time-of-flight mass spectrometry using infusion with crown ethers, *Rapid Commun. Mass Spectrom.*, 2011 26: 154-162); (Deperre, C.; McCord, B. Trace analysis of urea nitrate by liquid chromatography-UV/fluorescence, *Forensic Science International*, 2011 211(1) 76-82); (Tarvin, M; McCord, B; Mount, K; Miller, M L, Analysis of Hydrogen Peroxide Field Samples by HPLC/FD and HPLC/ED in DC Mode Forensic Sci. Int. 2011 209(1-3):166-72); (Tarvin, M.; McCord, B.; Mount, K.; Sherlach K; Miller, M L, Optimization of Two Methods for the Analysis of Hydrogen Peroxide: High Performance Liquid Chromatography with Fluorescence Detection and High Performance Liquid Chromatography with Electrochemical Detection in Direct Current Mode, *J. Chromatogr. A* 2010 1217(48) 7564-72); (Megan Bottegal; Gui-hua Lisa Lang; Mark Miller; Bruce McCord, Analysis of Ascorbic Acid-Based Black Powder Substitutes by High Performance Liquid Chromatography-Electrospray Ionization-Quadrupole Time-of-Flight Mass Spectrometry (HPLC-ESI-QToFMS), *Rapid* Communications in Mass Spectrometry 2010 24(9) 1377-1386); (Kristy G. Lahoda; Olivier L. Collin; John A. Mathis; Holly E. LeClair; Steven H. Wise and Bruce R. McCord, A Survey of Background Levels of Explosives and Related Compounds in the Environment, *J. Forensic Sciences*, 2008 53(4) 802-806); (Collin, O. L., Niegel, C. DeRhodes, K., McCord, B., Jackson, G., Fast GC of Explosive Compounds using a Pulsed Discharge Electron Capture Detector, *J Forensic Sciences,* 2006, 51 (4), 815-818); (Hopper, K.; McCord, B. "A Novel Method for Simultaneous Analysis of Cations and Anions in Inorganic Explosive Residue," *Talanta,* 2005, 67, 304-312); (Mathis, J.; McCord, B. The Analysis of High Explosives by Liquid Chromatography Electrospray Ionization Mass Spectrometry: Multiplexed Detection of Negative Ion Adducts, *Rapid Communications in Mass Spectrometry* 2005, 19(2), 99-104); (Mathis, J.; McCord, B. A Gradient Reversed Phase High Performance Liquid Chromatography-Electrospray Ionization Mass Spectrometric Method for the Comparison of Smokeless Powders *Journal of Chromatography A,* 2003, 988, 107-116); (Heramb, R.; McCord, B. Smokeless powders and their analysis, a brief review. *Forensic Science Communications* 2002, 4 (2), 1-7); (Wissinger, C. E.; McCord, B. R. A reversed phase HPLC procedure for smokeless powder comparison, *Journal of Forensic Sciences* 2002, 47 (1), 168-174); (Doyle, J. M.; Miller, M. L.; McCord, B. R.; McCollam, D. A.; Mushrush, G. W. A Multicomponent Mobile Phase for Ion Chromatography Applied to the Separation of Anions from the Residue of Low Explosives, Analytical Chemistry 2000, 72(10), 2303-2307); (Smith, K. D.; McCord, B. R.; MacCrehan, W. A.; Mount, K.; Rowe, W. F. Detection of Smokeless Powder Residue on Pipe Bombs by Micellar Electrokinetic Chromatography, *Journal of Forensic Sciences* 1999, 44(4), 789-794); Doyle, J. M.; McCord, B. R. Novel electrolyte for the analysis of cations in low explosive residue by capillary electrophoresis *Journal of Chromatography B* 1998, 714, 105-111); (McCord, B. R.; Hargadon, K.; Hall, K.; Burmeister, S. Forensic Analysis of Explosives using Ion Chromatographic Methods, *Analytica Chimica Acta* 1994, 288, 43-56); and (McCord, B. R.; Whitehurst, F. W. The Analysis and Characterization of TNT using Liquid Chromatography with Photodiode Array Detection, *Journal of Forensic Sciences* 1992, 37(6), 1574-1584). Each of these publications is hereby incorporated by reference in their entireties.

The subject invention is drawn to devices and methods for detection of explosives, e.g., improvised explosives or HMEs. In an embodiment of the subject invention, a paper microfluidic device (PMD) is used to detect explosives, such as improvised explosives and/or HMEs. The PMD can be used as an immediate-response field screening tool for explosives (e.g., improvised explosives and/or HMEs) and their constituent ions. Advantageously, a very small extraction volume can be used, such as 50 µL or less, for a sample. The sample can be used by personnel in the field for immediate information or by analysts in the laboratory to triage samples and prioritize analyses. In one embodiment, an extraction volume of 35 µL or about 35 µL is used as a sample.

According to several embodiments of the subject invention, paper microfluidics is used for detection of improvised explosives or HMEs. Paper microfluidics is a transformational technology that permits the development of very inexpensive analytical devices. In an embodiment of the subject invention, a design is printed in ink (e.g., wax-based ink) on paper (e.g., filter paper or chromatography paper). The channels (e.g., wax channels) in the paper direct a liquid sample toward one or more individual sections of the paper, which can contain at least one test reagent. The channels can be hydrophobic. In certain embodiments, one or more of the test reagents can be a colorimetric test reagent. In a particular embodiment, a nitrocellulose membrane can be used instead of paper.

Colorimetric spot tests are a fundamental technique that is known in various forms. Using physical and chemical properties of a chosen analyte, spot tests react to give a visible color change when the analyte of interest is present. Color spot tests may be presumptive or specific, and can be used according to the subject invention in the analysis of explosives. They may test for, e.g., intact compounds, ions, functional groups, metals, and/or enzymes. They may be based in classical wet chemistry methods, nanoparticle aggregation, or antibody/aptamer detection. Color test kits for the analysis of nitroaromatics, nitrate esters, and nitramines using spray reagents can be used. Spot tests for compounds such as urea nitrate and hydrogen peroxide can be used in embodiments of the subject invention.

Colorimetric bioassay techniques can also be employed for small molecules and ions. For example, perchlorate can be detected by colorimetric bioassay using perchlorate reductase enzyme and N-methyl phenazinium sulfate as a visualizing agent. A nitrate reduction test can be used to show whether bacteria can produce nitrate reductase enzyme to reduce nitrate to nitrite using sulfanilic acid and N,N-dimethyl-1-naphthalene. This technique, or a reverse thereof using nitrate reductase, can be used.

Functionalized gold nanoparticles are another avenue of detection that can be used in embodiments of the subject invention. While most commonly used in biomedical applications and DNA analysis, by adding a suitable reagent during the synthesis process, it is possible to create functionalized nanoparticles to detect a variety of compounds by the aggregation or disaggregation of gold nanoparticles that results in a characteristic red-to-blue color change. Functionalized gold nanoparticles can be used for the detection of, among other things, aluminum, hydrogen peroxide, and reducing sugars including sucrose (table sugar).

Figure 3:
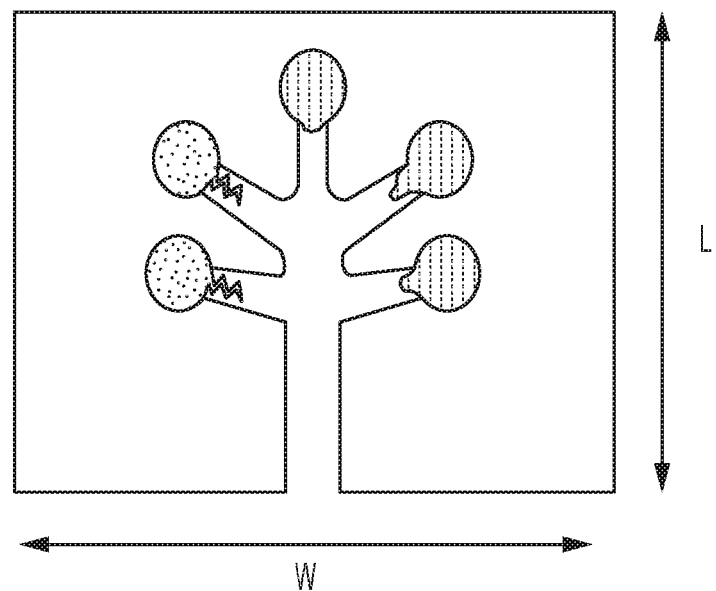
FIG. 3 shows a PMD according to an embodiment of the subject invention.

By using multiple indicators for the same compound, a user's ability to discriminate between different shades and intensities of color that indicate concentration is increased, and data can be more accurately interpreted. In the case of ions and small molecules, multiple indicators for the same compound can also help avoid a false positive result since the interferences for tests using different reagents or mechanisms for the same analyte are unlikely to be the same for both systems. Referring to FIG. 3, a PMD can include multiple redundant tests on a single device. Change in the chemistry can permit detection of the same compound with differing responses. The example in FIG. 3 shows simultaneous detection of two different compounds using five channels, two for one compound and three for the other. In FIG. 3, W represents the width of the PMD, and L represents the length (or height).

The area of a PMD according to embodiments of the subject invention can be less than 4.5 square centimeters ($cm^2$). The area of a PMD according to embodiments of the subject invention can be less than, for example, 50 cm$^2$, 20 cm$^2$, 10 cm$^2$, 7 cm$^2$, 6.5 cm$^2$, 6 cm$^2$, 5 cm$^2$, 4.5 cm$^2$, 4.25 cm$^2$, 4.2 cm$^2$, 4.1 cm$^2$, 4 cm$^2$, 3.5 cm$^2$, 3 cm$^2$, 2 cm$^2$, 1 cm$^2$, or 0.5 cm$^2$. A PMD according to embodiments of the subject invention can have a width and/or length (height) of 2 centimeters (cm), 2.5 cm, 2.54 cm, or about 2 cm. A PMD according to embodiments of the subject invention can have a width and/or length (height) of, for example, 0.5 cm, 1 cm, 1.5 cm, 2 cm, 2.5 cm, 2.54 cm, 3 cm, 4 cm, 5 cm, 6 cm, 7 cm, 8 cm, 9 cm, or 10 cm. In one embodiment, a PMD has a width of about 2 cm and a length of about 2 cm, giving an area of about 4 cm$^2$.

In certain embodiments, a single PMD can perform multiple analyses by having multiple channels and multiple test reagents. For example, a paper microfluidic device can perform, two, three, four, five, six, seven, eight, nine, 10, or more analyses on one device. These analyses can be performed simultaneously or essentially simultaneously (i.e., after providing a single sample to a PMD and allowing it to travel through channels to multiple testing points). Such a PMD can be made of paper (e.g., chromatography paper) and wax, and can include small quantities of test reagents. Each of these components is inexpensive; thus, a PMD according to embodiments of the subject invention can perform multiple simultaneous analyses (e.g., 2, 5, 10, or more) while costing only pennies. A PMD of the subject invention is also easily stored for long-term performance. Due to these factors, PMDs of the subject invention are very advantageous for on-site forensic testing and screening for improvised explosives and HMEs.

In an embodiment, a PMD can have a path that branches out into two or more paths. Each branched path can lead to a testing spot, which can include a test reagent. Referring again to FIG. 3, a PMD having such branched paths is shown. Though a PMD with five branches is shown, this should not be construed is limiting. For example, PMDs having two, three, four, six, etc. branches can be used.

PMDs of the subject invention provide police and forensic evidence collection teams an easily-stored and reliable tool for presumptive testing of unknown evidence. The devices can be easily and cheaply manufactured and take up no more space than a package of cigarette papers. The low cost and easy portability allow for an analyst or crime scene response team member to carry a kit capable of instant identification of unknown or hazardous compounds. PMDs of the subject invention can also be used in the analysis of seized drugs from, for example, clandestine manufacturing sites or in a Customs setting in a port.

In several embodiments, a PMD is configured for the presumptive detection of explosives (e.g., improvised explosives or HMEs). The device can be configured to analyze samples from both pre- and post-blast residues.

In an embodiment, a PMD includes colorimetric spots for forensic explosives analysis. Colorimetric test reagents are present on the device, and such colorimetric test reagents can be present at or near the ends of channels formed in the device. Examples of colorimetric test reagents that can be included on a device include Greiss reagents, diphenylamine reagents, p-dimethylaminocinnamaldehyde (p-DMAC), and ammonium titanyl oxalate. For example, Greiss and diphenylamine reagents can be used to test for organic and inorganic nitrates, p-DMAC can be used to test for urea nitrate, and ammonium titanyl oxalate can be used to test for peroxides. These reagents are given for exemplary purposes only and should not be construed as limiting.

In certain embodiments, test reagents are spotted in an analysis lane of a PMD. When the solvent containing the sample moves through the printed lane, it dissolves the reagents, allowing them to react with the sample and generate a color change. The PMD can combine a set of tests for multiple compounds, including, for example, chlorates, nitrates, organic nitrates, peroxides, fertilizer-based explosives, and/or high explosives. Such a set of tests can be combined on a single piece of paper. The device can be configured for long-term storage with sensitive and reliable detection of the relevant materials.

In several embodiments, a PMD is configured to provide fast and sensitive colorimetric detection of the constituents of improvised explosives or HMEs in pre- or post-blast settings. The PMD can be used as a first-line response and presumptive field identification tool for the presence of improvised explosives or HMEs before samples are sent to a central laboratory for analysis. In a laboratory setting, analysts can use a PMD of the subject invention to triage evidence and prioritize instrumental analyses to maximize the amount of information generated from a limited sample volume.

A PMD of the subject invention can be fabricated by, for example, plasma etching, photolithography, PDMS printing, or wax printing. In a preferred embodiment, a PMD is fabricated by wax printing. A PMD made by photolithography can be more finely resolved than one made by a wax printing process, but the wax printing process does not require the specialized equipment and personnel trained in the maintenance and use of that equipment that the other processes do.

Figure 1B:
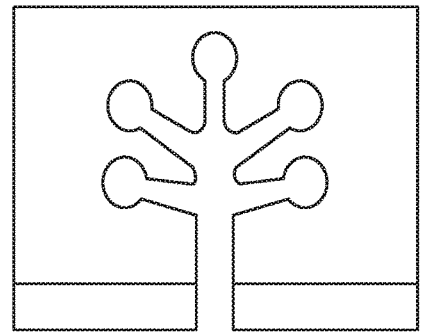
Figure 1C:
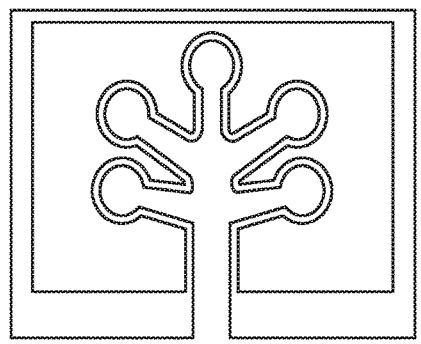
Figure 1D:
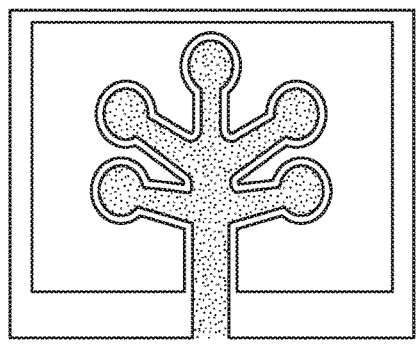

In an embodiment, a PMD is fabricated by printing a wax pattern onto a paper substrate (e.g., filter paper or chromatography paper), and the paper substrate can be heated so the liquid wax penetrates the paper substrate. This creates hydrophobic barriers that function as lanes or channels for a liquid sample to move along as it is routed to one or more detection zones. This process is depicted in FIGS. 1A-1D. The design can be conceptualized (FIG. 1*a*), and the wax can be printed onto the paper substrate (FIG. 1*b*). The paper substrate can then be heated so the liquid wax penetrates the paper substrate and creates hydrophobic barriers (FIG. 1*c*). Then, a liquid sample can move along the resulting as lanes or channels to one or more detection zones (FIG. 1*d*).

The natural wicking action of the paper as it draws up the liquid sample takes the place of a pump, and test reagents placed precisely within the pattern give an immediate, visible color change showing the presence of an analyte.

In an embodiment, a PMD can have a three-dimensional (3-D) configuration. By using a device with a 3-D configuration, the number of tests incorporated can be increased while keeping reagent volume to a minimum. This can be accomplished using a chip, which can be produced on a single sheet of flat paper, which is then folded in a prescribed way to line up the channels and reservoirs in the different layers. The sample solution can be introduced into the reservoirs on the top layer of the device. The sample solution can be carried through the layers of the device by capillary action to interact with the test reagents. In a particular embodiment, the folded PMD is inserted into a metal frame to ensure the channels and reservoirs do not shift during use.

Figures 2A, 2B, 2C:
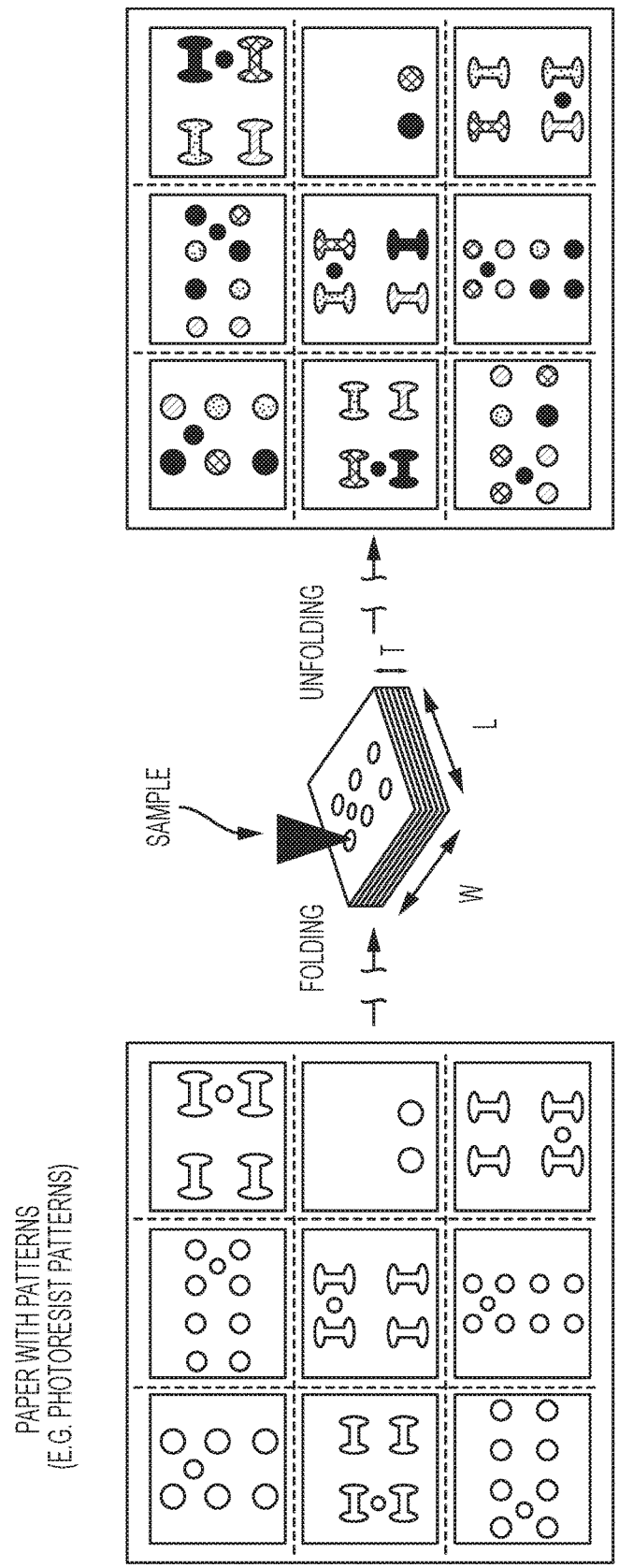
FIGS. 2A-2C show examples of the movement of samples through a three-dimensional PMD according to an embodiment of the subject invention.

Referring to FIGS. 2A-2C, an example of the movement of samples through a 3-D PMD is depicted. When the analysis is complete, the PMD can be removed from the frame (if a frame was used) and unfolded to view the results. For clarity, the PMD can be marked with indicators to identify each test. FIG. 2*a* shows an example of a patterned paper. FIG. 2*b* shows a folded 3-D PMD which can then be injected with a test solution (sample). FIG. 2*c* shows an example of results of a test, where colors indicate whether a target analyte is present. Though the boxes in FIGS. 2a and 2c may appear to be different sizes and/or shapes, in a 3-D PMD they are actually all approximately the same size and shape. In FIG. 2b, W represents the width of the 3-D PMD, L represents the length of the 3-D PMD, and T represents the thickness of the 3-D PMD.

The volume of a 3-D PMD according to embodiments of the subject invention can be less than 4 cubic centimeters (cc). The volume of a 3-D PMD according to embodiments of the subject invention can be less than, for example, 20 cc, 15 cc, 10 cc, 7 cc, 5 cc, 4 cc, 3.5 cc, 3.2 cc, 3 cc, 2 cc, 1 cc, 0.5 cc, or 0.2 cc. A 3-D PMD according to embodiments of the subject invention can have a width and/or length of 2.5 cm, 2.54 cm, or about 2.5 cm. A 3-D PMD according to embodiments of the subject invention can have a width and/or length of, for example, 0.5 cm, 1 cm, 1.5 cm, 2 cm, 2.5 cm, 2.54 cm, 3 cm, 4 cm, 5 cm, 6 cm, 7 cm, 8 cm, 9 cm, or 10 cm. A 3-D PMD according to embodiments of the subject invention can have a thickness of 0.5 cm or about 0.5 cm. A 3-D PMD according to embodiments of the subject invention can have a thickness of, for example, 0.1 cm, 0.5 cm, 1 cm, 1.5 cm, 2 cm, 2.5 cm, 2.54 cm, 3 cm, 4 cm, or 5 cm. In one embodiment, a 3-D PMD has a width of about 2.5 cm, a length of about 2.5 cm, and a thickness of about 0.5 cm, giving a volume of about 3.125 cc.

In one embodiment, the volume of a sample provided to a 3-D PMD is about 75 µL.

In an embodiment, a kit can include a PMD as described herein. The PMD may have test reagents already present for spot tests or may have no test reagents present on the PMD. The kit may additionally include one or more test reagents for testing for compounds of explosives (e.g., improvised explosives and HMEs). A user can apply the test reagents to the testing sites of a PMD that does not already have the test reagents present.

In an embodiment, a method of testing a sample for explosives (e.g., improvised explosives and/or HMEs) can include providing the sample to a PMD as described herein. The sample can be, for example, dissolved in a suitable solvent and applied to the PMD, though embodiments are not limited thereto. The sample can be provided to the PMD in a very small amount. In various embodiments, the amount of the sample provided to the PMD can be, for example, any of the following values, about any of the following values, less than any of the following values, or at least any of the following values (all numerical values are in µL): 0.001, 0.01, 0.1, 0.5, 1, 2, 3, 4, 5, 6, 7, 8, 9, 10, 15, 20, 25, 30, 35, 40, 45, 50, 55, 60, 70, 75, 80, 90, 100, 110, 120, 130, 140, 150, or 200. For example, the sample can be provided to the PMD in an amount of 75 about 75 µL, less than 75 µL, 50 µL, about 50 µL, less than 50 µL, 35 µL, about 35 µL, or less than 35 µL. In some embodiments, the amount of solvent (having the sample dissolved therein) required to transport the sample to the test spot(s) can be 50-200 µL.

Examples of solvents that can be used include, but are not limited to, water, crown ethers, acetone, ethanol, methanol, dimethyl sulfoxide (DMSO), dimethylformaldehyde (DMF), and any combination thereof.

In an embodiment, a sample can be tested using a PMD as described herein, and the results can be photographed. The image or images can be transmitted to a remote location, e.g., to a laboratory having an expert who evaluates the results and responds with a course of treatment if it is required. This way, an expert need not be on site to interpret the results of the tests. Such a picture can be taken with any suitable device, such as a camera of a mobile phone. In a further embodiment, the image or images can be accompanied by one or more images of standards run in the field, or such standard run images can be provided before or after the image or images of the PMD test.

Embodiments of the subject invention can advantageously allow for the colorimetric detection of one or more analytes simultaneously or essentially simultaneously. Certain embodiments can also have redundant testing for one or more analytes simultaneously or essentially simultaneously. This technology is very advantageous for first responders and forensic professionals who may encounter improvised explosives and HMEs in routine work. PMDs of the subject invention can detect a wide variety of compounds with very dissimilar properties. The use of PMDs in the field with all their attendant benefits—speed, low cost, portability, specificity, sensitivity, ease of use, and ability to generate results without electricity or specialized equipment—is limited only by the choice of compounds one wishes to detect. PMDs of the subject invention are also advantageous for smaller labs that lack the necessary funds or caseload to justify the dedicated equipment (e.g., ion chromatography and specialized negative ion GC/MS systems and capillaries) necessary for explosives analysis.

Embodiments of the subject invention provide police and forensic evidence collection teams easily-stored and reliable tools for presumptive testing of unknown evidence. PMDs of the subject invention can be easily and cheaply manufactured and are very small and portable (e.g., a group may be about the size of a package of cigarette papers, or smaller). The low cost and easy portability allows analysts and crime scene response team members to carry a kit capable of instant identification of unknown or hazardous compounds. PMDs of the subject invention can also be applied in the determination of seized drugs from, for example, clandestine manufacturing sites or a Customs setting in a port.

Figure 8A:
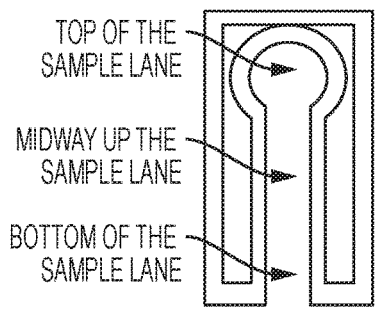
FIG. 8A shows an image of a PMD according to an embodiment of the subject invention.
Figure 8B:
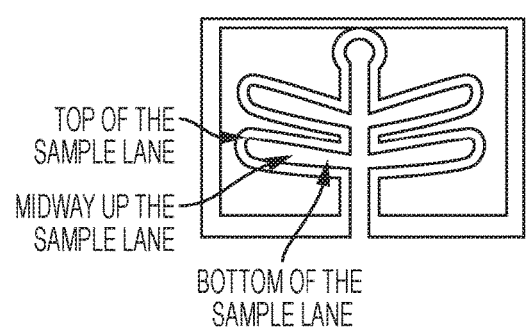
FIG. 8B shows an image of a PMD according to an embodiment of the subject invention.
Figure 9:
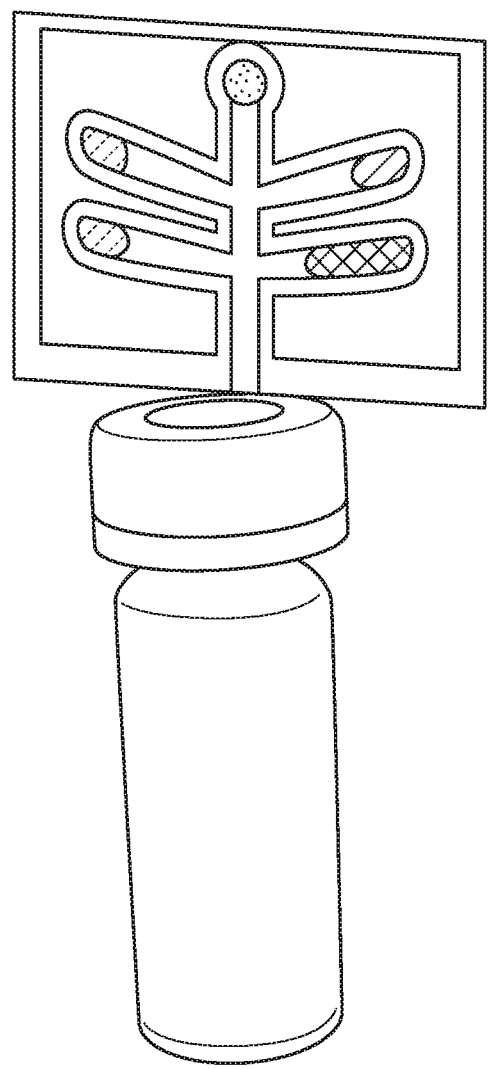
FIG. 9 shows an image of a PMD according to an embodiment of the subject invention.
Figure 17A:
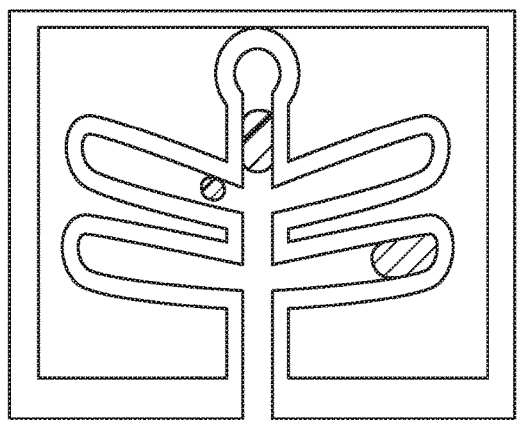
FIG. 17A shows an image of a PMD according to an embodiment of the subject invention.
Figure 17B:
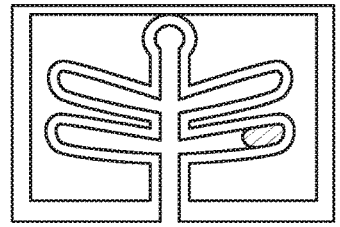
FIG. 17B shows an image of a PMD according to an embodiment of the subject invention.

FIGS. 8, 9, and 17 show images of PMDs according to embodiments of the subject invention. Referring to FIG. 8A, in an embodiment, a PMD can have a single channel or lane. Referring to FIG. 8B, in an embodiment, a PMD can have five channels. Referring to FIG. 9, a PMD can be inserted into a solution (e.g., in a vial) including the sample dissolved in a solvent. Referring to FIG. 17A, in an embodiment, a five-channel PMD can be configured for detection of inorganic explosives detection with a total run time (for the testing) of about 18 minutes. Referring to FIG. 17B, in an embodiment, a five-channel PMD can be configured for detection of inorganic explosives detection with a total run time (for the testing) of about five minutes and can have a much smaller size than the PMD shown in FIG. 17A.

Following are examples that illustrate procedures for practicing the invention. These examples should not be construed as limiting. All solvent mixture proportions are by volume unless otherwise noted.

EXAMPLE 1

Figure 4:
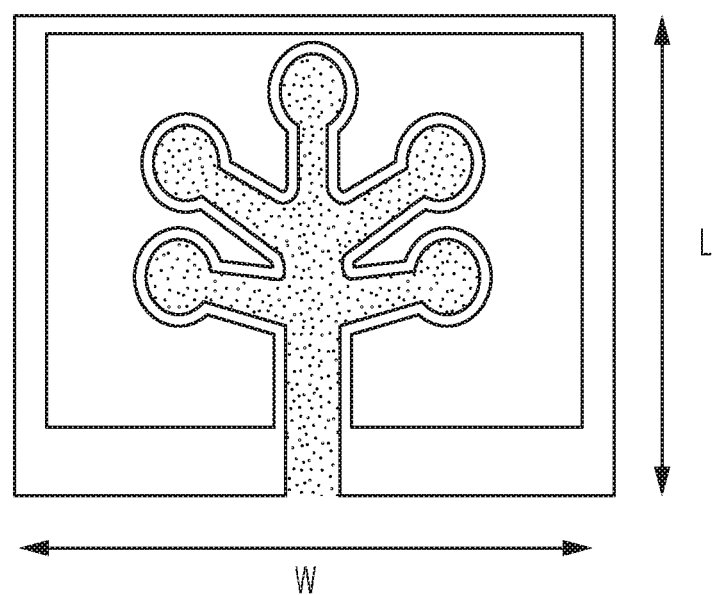
FIG. 4 shows a PMD according to an embodiment of the subject invention.

A design in wax ink was printed on an 8.5-inch×11-inch sheet of chromatography paper. To create the hydrophobic channels in the paper, the wax was heated and reflowed into the paper by running the printed sheet through a standard office document laminator. The finished chips were then tested using a water solution of eosin Y indicator to ensure the wax had penetrated the paper completely. A picture of this PMD is shown in FIG. 4. Referring to FIG. 4, this particular PMD has indicating dye and can perform five simultaneous tests. The combination of heat and pressure the laminator applies to the printed chip creates hydrophobic sample lanes.

Figure 5:
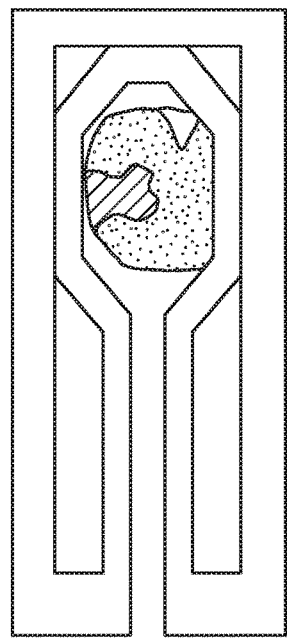
FIG. 5 shows the results of a test of p-DMAC as a test reagent for urea nitrate.
Figure 6:
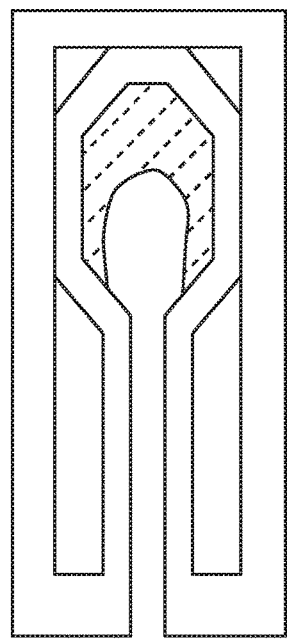
FIG. 6 shows the results of a test of ammonium titanyl oxalate as a test reagent for peroxide.

Several colorimetric tests were evaluated for their fitness for use in PMDs. Some reagents, such as p-DMAC for the detection of urea nitrate, are amenable to dissolution in a small amount of solvent and direct spotting on the PMD. Likewise, peroxide can be detected by the use of ammonium titanyl oxalate on a paper substrate. Referring to FIG. 5, urea nitrate was detected with p-DMAC, giving a red color. Referring to FIG. 6, peroxide was detected with ammonium titanyl oxalate, giving a yellow color.

Figure 7:
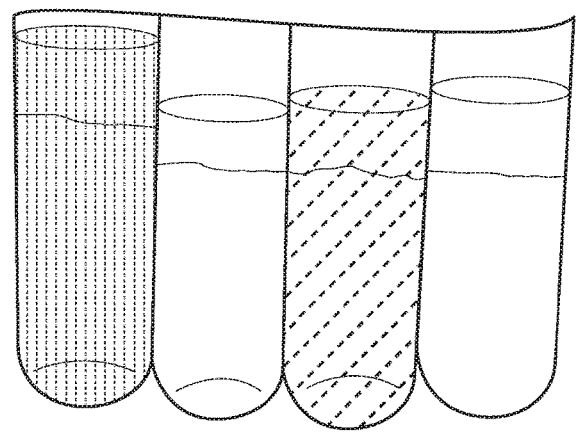
FIG. 7 shows the results of a test for ammonium ion using different solvents.

Other tests were also evaluated on a paper substrate. A test for ammonium ion gave a positive result when the ammonium source was dissolved in various solvents. Referring to FIG. 7, ammonium ion was detected in deionized water (far left), acetone (second from left), and a mixture of 95% acetone and 5% methyl cellosolve (far right). A negative result was obtained using methanol as a solvent.

Test reagents were spotted in analysis lane of the PMD. Thus, if a solvent containing a sample were moved through the printed lane, it would dissolve the reagents, allowing them to react with the sample and generate a color change. The PMD combined a set of tests for urea nitrate and peroxide.

EXAMPLE 2

Referring to FIGS. 10A and 10B, a five-channel PMD was configured to test for $NH_4^+$, $NO_3^-$, $NO_2^-$, $ClO_3^-$, and $ClO_4^-$. FIG. 10B shows the PMD of FIG. 10A after a testing time of 18 minutes. Color change started after about five minutes.

EXAMPLE 3

Five single-channel PMDs were tested. All of the PMDs were prepared using 2 µL of each reagent spotted onto the PMD. Explosive compounds were inserted in a plastic vial with 1000 ppm of the compound dissolved in deionized water and deionized water was used as a blank. The reaction time for the single lane PMDs was about five minutes.

FIGS. 11A-11B show the results the left side of each figure shows the channel after testing the blank, and the right side of each figure shows the channel testing the explosive compound. Referring to FIG. 11A, a PMD was tested for chlorate ($ClO_3^-$) using aniline sulfate and 50% sulfuric acid as reagents. The test spot changed from colorless to dark green when the explosive compound was tested. Referring to FIG. 11B, a PMD was tested for nitrite ($NO_2^-$) using the Greiss test with sulphanilic acid and 1-napthylamine as reagents. The test spot changed from colorless to orange/brown when the explosive compound was tested. Referring to FIG. 11C, a PMD was tested for ammonium ($NH_4^+$) using Nessler's Reagent as a reagent. The test spot changed from pale yellow to orange/brown when the explosive compound was tested. Referring to FIG. 11D, a PMD was tested for nitrate ($NO_3^-$) using (1) a paste of saturated tehalose solution with solid reducing mixture of sulfanilic acid, sodium acetate, and zinc powder, (2) 20% sulfuric acid, and (3) 1-napthol as reagents. The test spot changed from colorless to orange when the explosive compound was tested. Referring to FIG. 11E, a PMD was tested for perchlorate ($ClO_4^-$) using 0.05% methylene blue as a reagent. The test spot changed from pale blue to purple when the explosive compound was tested.

EXAMPLE 4

Figure 12A:
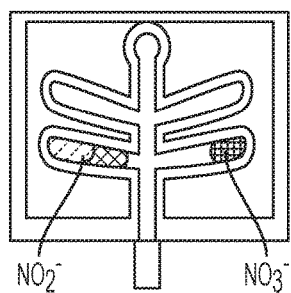
FIG. 12A shows an image of a PMD according to an embodiment of the subject invention.
Figure 12B:
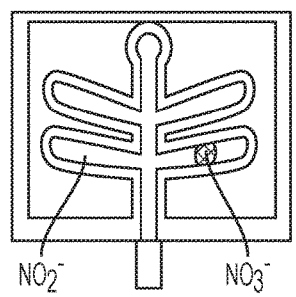
FIG. 12B shows an image of a PMD according to an embodiment of the subject invention.
Figure 12C:
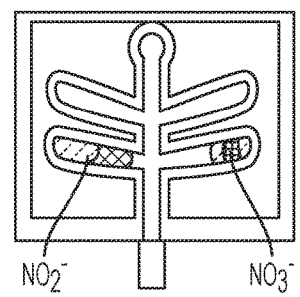
FIG. 12C shows an image of a PMD according to an embodiment of the subject invention.

Referring to FIGS. 12A-12C, five-channel PMDs were configured to test for $NO_3^-$ and $NO_2^-$. FIG. 12A shows a PMD after the test run with 1000 ppm potassium nitrite in deionized water. The nitrate test generated a dark purple color while the nitrite test produced an orange-brown color. FIG. 12B shows a PMD after the test run with 1000 ppm potassium nitrate in deionized water. The nitrate test generated an orange color while the nitrite test did not show any color change. FIG. 12C shows a PMD after the test run with 1000 ppm mixture of potassium nitrate and potassium nitrite. The nitrite test produced an orange-brown color while the nitrate test showed a dark purple and orange color.

EXAMPLE 5

Figure 13A:
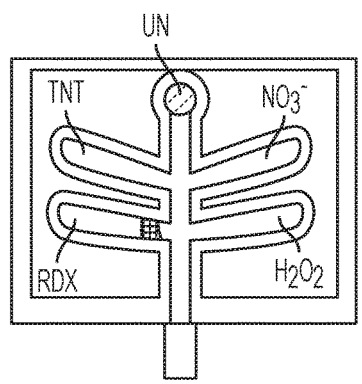
FIG. 13A shows an image of a PMD according to an embodiment of the subject invention.
Figure 13B:
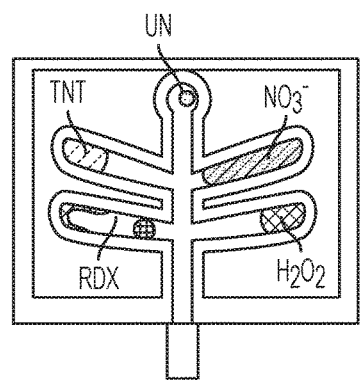
FIG. 13B shows an image of a PMD according to an embodiment of the subject invention.

Referring to FIGS. 13A and 13B, a five-channel PMD was configured to test for RDX, TNT, UN, $NO_3^-$, and $H_2O_2$. FIG. 13B shows the PMD of FIG. 13A after the test. A mixture of HMX, TNT, urea nitrate, and hydrogen peroxide in 50% acetone/50% water was tested. Color changes began to occur after five minutes with a total run time of approximately 18 minutes for complete visualization.

EXAMPLE 6

Five single-channel PMDs were tested. All of the PMDs were prepared using 2 µL of each reagent spotted onto the PMD. Explosive compounds were inserted in a plastic vial with 1000 ppm of the compound dissolved in 50% acetone/50% water and 50% acetone/50% water was used as a blank. The reaction time for the single lane PMDs was about five minutes.

Figure 14A:
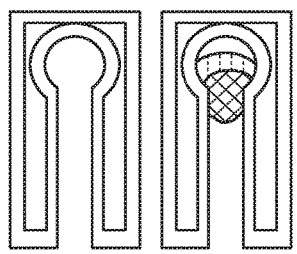
FIG. 14A shows an image of a PMD according to an embodiment of the subject invention.
Figure 14B:
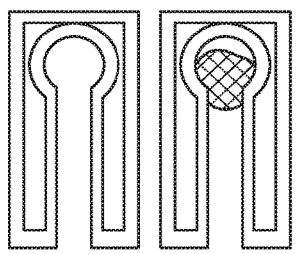
FIG. 14B shows an image of a PMD according to an embodiment of the subject invention.
Figure 14C:
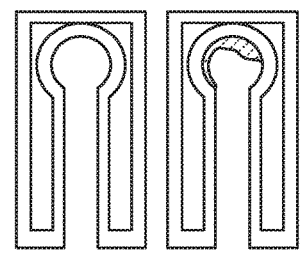
FIG. 14C shows an image of a PMD according to an embodiment of the subject invention.
Figure 14D:
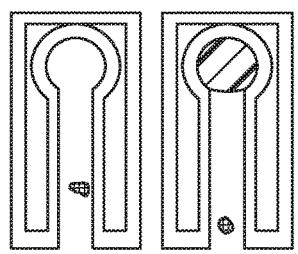
FIG. 14D shows an image of a PMD according to an embodiment of the subject invention.
Figure 14E:
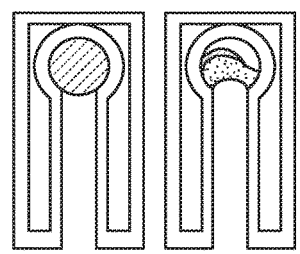
FIG. 14E shows an image of a PMD according to an embodiment of the subject invention.

FIGS. 14A-14B show the results; the left side of each figure shows the channel after testing the blank, and the right side of each figure shows the channel testing the explosive compound. Referring to FIG. 14A, a PMD was tested for nitrate ($NO_3^-$) using (1) a paste of saturated tehalose solution with solid reducing mixture of sulfanilic acid, sodium acetate, and zinc powder, (2) 20% sulfuric acid, and (3) 1-napthol as reagents. The test spot changed from colorless to orange when the explosive compound was tested. Referring to FIG. 14B, a PMD was tested for trinitrotoluene (TNT) using 1.5 M potassium hydroxide as a reagent. The test spot changed from colorless to pink/red when the explosive compound was tested. Referring to FIG. 14C, a PMD was tested for hydrogen peroxide ($H_2O_2$) using ammonium titanyl oxalate as a reagent. The test spot changed from colorless to yellow when the explosive compound was tested. Referring to FIG. 14D, a PMD was tested for RDX, HMX, and PETN using (1) zinc powder in 50% acetic acid, (2) sulfanilic acid, and (3) 1-napthylamine as reagents. The test spot changed from colorless to pink when the explosive compound was tested. Referring to FIG. 14E, a PMD was tested for urea nitrate (UN) using para-dimethylaminocinnamaldehyde as a reagent. The test spot changed from yellow to red when the explosive compound was tested.

EXAMPLE 7

Figure 15A:
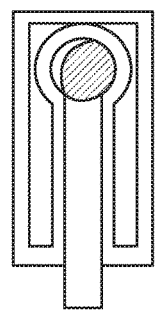
FIGS. 15A-15C show images of a PMD according to an embodiment of the subject invention.
Figure 15B:
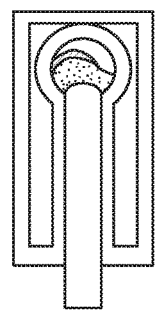
Figure 15C:
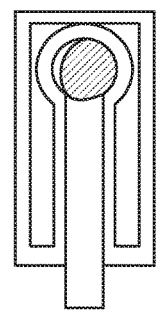

Referring to FIGS. 15A-15C, single-channel PMDs were configured to test for UN. FIG. 15A shows the results of a blank run with just 50% acetone/50% water. FIG. 15B shows the results of a test run with 1000 ppm UN in 50% acetone/50% water producing a red color. FIG. 15C shows the results of a test run with 1000 ppm urea in 50% acetone/50% deionized water.

EXAMPLE 8

Figure 16A:
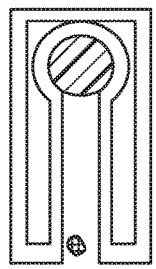
FIGS. 16A-16B show images of a PMD according to an embodiment of the subject invention.
Figure 16B:
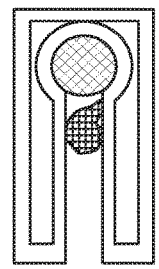

Referring to FIGS. 16A and 16B, single-channel PMDs were configured to test for RDX/HMX/PETN. FIG. 16A shows the results of a test run with 1000 ppm HMX in 50% acetone/50% water producing a pink color change. FIG. 15B shows the results of a test run with 1000 ppm potassium nitrate in 50% acetone/50% water producing a noticeably different orange color change.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A paper microfluidic device (PMD), comprising:
   a paper substrate;
   one or more hydrophobic channels on the paper substrate; and
   a test reagent provided at a test spot of at least one of the hydrophobic channels;
   wax on the paper substrate, said wax outlining and surrounding each hydrophobic channel of the one or more hydrophobic channels except a portion of each hydrophobic channel that receives a test sample when in use; and
   a tab protruding from the paper substrate and comprising a proximal end and a distal end opposite to the proximal end, said tab configured such that the distal end contacts a test sample when in use,
   the distal end of the tab being free from wax, and
   the test reagent being configured to test for explosives.

2. The PMD according to claim 1, comprising at least two hydrophobic channels on the paper substrate, wherein each hydrophobic channel comprises a test spot, and wherein each test spot comprises a test reagent configured to test for at least one of improvised explosives and homemade explosives.

3. The PMD according to claim 2, wherein at least two of the test spots have the same test reagent provided thereon.

4. The PMD according to claim 2, wherein a first hydrophobic channel of the at least two hydrophobic channels comprises a first test spot having a first test reagent configured to test for at least one of improvised explosives and homemade explosives,
   wherein a second hydrophobic channel of the at least two hydrophobic channels comprises a second test spot having a second test reagent configured to test for at least one of improvised explosives and homemade explosives, and
   wherein the first test reagent is different from the second test reagent.

5. The PMD according to claim 4, wherein a third hydrophobic channel of the at least two hydrophobic channels comprises a third test spot having a third test reagent configured to test for at least one of improvised explosives and homemade explosives, and wherein the third test reagent is different from the first test reagent and the second test reagent.

6. The PMD according to claim 1, comprising a main hydrophobic channel and a plurality of secondary hydrophobic channels branching off from the main hydrophobic channel, wherein each secondary hydrophobic channel comprises a test spot having a test reagent configured to test for at least one of improvised explosives and homemade explosives.

7. The PMD according to claim 1, wherein each hydrophobic channel is a wax channel, and wherein the paper substrate is filter paper or chromatography paper.

8. The PMD according to claim 1, wherein the area of the paper substrate having the one or more hydrophobic channels is less than 4.5 square centimeters ($cm^2$).

9. The PMD according to claim 1, wherein the test reagent is a colorimetric test reagent.

10. A method of testing a sample for explosives, comprising:
    providing the sample to the PMD according to claim 1.

11. The method according to claim 10, further comprising dissolving the sample in a solvent to give a sample solution,
    wherein providing the sample to the PMD comprises providing the sample solution to the PMD in a volume of less than 75 µL.

12. The method according to claim 11, further comprising:
    photographing the PMD after the sample solution has interacted with the test reagent to give a result image; and
    transmitting the result image to a remote location.

13. The method according to claim 10, further comprising dissolving the sample in a solvent to give a sample solution,
    wherein providing the sample to the 3-D PMD comprises injecting the sample solution into a top layer of the 3-D PMD in a volume of less than 75 µL.

14. The PMD according to claim 1, wherein the test reagent comprises at least one of the following: functionalized gold nanoparticles; a mixture of perchlorate reductase and N-methyl *phenazinium* sulfate; or a mixture of sulfanilic acid and N,N-dimethyl-1-naphthalene.

\* \* \* \* \*